United States Patent
Nakajima et al.

(10) Patent No.: US 11,266,591 B2
(45) Date of Patent: Mar. 8, 2022

(54) OIL-IN-WATER TYPE EMULSION COSMETIC

(71) Applicant: SHISEIDO COMPANY, LTD., Tokyo (JP)

(72) Inventors: Minori Nakajima, Yokohama (JP); Keita Nishida, Yokohama (JP); Yurika Watanabe, Yokohama (JP); Daiki Arai, Yokohama (JP); Taichi Harada, Yokohama (JP)

(73) Assignee: SHISEIDO COMPANY, LTD., Tokyo (JP)

( * ) Notice: Subject to any disclaimer, the term of this patent is extended or adjusted under 35 U.S.C. 154(b) by 0 days.

(21) Appl. No.: 16/649,342

(22) PCT Filed: Sep. 28, 2018

(86) PCT No.: PCT/JP2018/036249
§ 371 (c)(1),
(2) Date: Mar. 20, 2020

(87) PCT Pub. No.: WO2019/065963
PCT Pub. Date: Apr. 4, 2019

(65) Prior Publication Data
US 2020/0289400 A1    Sep. 17, 2020

(30) Foreign Application Priority Data
Sep. 29, 2017 (JP) .............................. JP2017-191350

(51) Int. Cl.
*A61K 8/92* (2006.01)
*A61K 8/06* (2006.01)
*A61K 8/73* (2006.01)
*A61Q 17/04* (2006.01)

(52) U.S. Cl.
CPC .............. *A61K 8/922* (2013.01); *A61K 8/062* (2013.01); *A61K 8/731* (2013.01); *A61Q 17/04* (2013.01)

(58) Field of Classification Search
None
See application file for complete search history.

(56) References Cited

FOREIGN PATENT DOCUMENTS

| | | |
|---|---|---|
| JP | 2003-073226 | 3/2003 |
| JP | 2007-169185 | 7/2007 |
| JP | 2011-136965 | 7/2011 |
| JP | 2011-136966 | 7/2011 |
| JP | 2011136965 A * | 7/2011 |
| JP | 2012-140334 | 7/2012 |
| JP | 2014-101335 | 6/2014 |
| JP | 2015-120682 | 7/2015 |

OTHER PUBLICATIONS

PCT/JP2018/036249, International Search Report (ISR) and Written Opinion (WO), dated Dec. 4, 2018, 11 pages—English, 10 pages—Japanese.

* cited by examiner

*Primary Examiner* — Nannette Holloman
(74) *Attorney, Agent, or Firm* — Andrew F. Young; Nolte Lackenbach Siegel

(57) ABSTRACT

An oil-in-water-type emulsion cosmetic contains an ultraviolet ray scattering agent and which has preparation stability in a system where a water-soluble alkyl-substituted polysaccharide derivative and another emulsifying agent coexist is further improved. The oil-in-water-type emulsion cosmetic containing (A) a water-soluble alkyl-substituted polysaccharide derivative, (B) a nonionic surfactant and (C) an ultraviolet ray scattering agent, wherein the blend ratio [(A)/(B)] of the water-soluble alkyl-substituted polysaccharide derivative (A) to the nonionic surfactant (B) is 1.54 or less, and the blend ratio [(A)/(C)] of the water-soluble alkyl-substituted polysaccharide derivative (A) to the ultraviolet ray scattering agent (C) is 0.02 or less.

6 Claims, No Drawings

OIL-IN-WATER TYPE EMULSION COSMETIC

CROSS REFERENCE TO RELATED APPLICATIONS

This application relates to and claims priority as a § 371 national phase, from PCT/JP2018/036249 filed Sep. 28, 2018, the entire contents of which are incorporated herein by reference, which in turn claims priority from JP 2017-191350 filed Sep. 29, 2017.

FIGURE SELECTED FOR PUBLICATION

None

TECHNICAL FIELD

The present invention relates to an oil-in-water emulsion cosmetic, particularly a sunscreen cosmetic, comprising an ultraviolet absorber (UV absorber) and an ultraviolet scattering agent (UV scattering agent), wherein the cosmetic is excellent in stability and texture while having high ultraviolet blocking capability (high SPF and PA).

BACKGROUND ART

An oil-in-water-type emulsion cosmetic has widely been used for cosmetics as a base giving fresh and light feeling on use as compared with a water-in-oil-type emulsion. When the oil-in-water emulsion base having such characteristics is used for a sunscreen cosmetic, an oil-soluble UV absorber and/or an UV scattering agent having hydrophobic surface is generally contained in an internal phase (oil phase).

It is conventionally known that when a powder, particularly a hydrophobically treated powder, is contained in an internal phase (oil phase) of an oil-in-water emulsion cosmetic, the emulsion system tends to become unstable. However, a few improvements, such as stabilization by admixing a water-soluble thickening agent into an external phase (water phase) and preventing aggregation of powder by introducing a dispersant into an internal phase (oil phase), have effectively been made.

For example, Patent Document 1 discloses an oil-in-water emulsion cosmetic in which a hydrophobically treated powder is stably contained by incorporating an acrylic acid-derived polymer and an alkyl-modified water-soluble cellulose ether. It is known that water-soluble alkyl-substituted polysaccharide derivatives including the alkyl-modified water-soluble cellulose ether used in this Patent Document 1 also contribute to stabilization of 2-(4-diethylamino-2-hydroxybenzoyl) benzoic acid hexyl ester that is an UV absorber having low solubility (Patent Documents 2 and 3).

Further, a cosmetic comprising a combination of a water-soluble alkyl-substituted polysaccharide derivative and a specific oil has been proposed for solving a problem of skin dryness attributed to a large amount of silicone oil contained in order to improve dispersibility of a UV scattering agent having hydrophobically surface treated with silicone, (Patent Document 4). There is also an example in which a unique fresh feeling on use has been achieved by containing a water-soluble alkyl-substituted polysaccharide derivative (hydrophobically modified alkyl cellulose) together with a predetermined amount of an oil and a water phase thickening agent having low salinity tolerance (Patent Document 5). It is thought that in these cosmetics, the water-soluble alkyl-substituted polysaccharide derivative functions also as an emulsifier and in addition there is no indication with regard to specific example of any other emulsifier.

CITATION LIST

Patent Document

JP 2012-140334 A
JP 2011-136965 A
JP 2011-136966 A
JP 2014-101335 A
JP 2015-120682 A

SUMMARY OF INVENTION

Technical Problem

As described above, it is known that the water-soluble alkyl-substituted polysaccharide derivative can contribute to stabilization of formulation and improvement in texture of oil-in-water emulsion sunscreen cosmetics. However, when the water-soluble alkyl-substituted polysaccharide derivative coexists with another emulsifying agent, particularly a nonionic surfactant, in an oil-in-water emulsion cosmetic exerting a high ultraviolet blocking effect (high SPF and high PA), stability of the cosmetic sometimes becomes insufficient. Accordingly, the present invention addresses the problem of providing an oil-in-water emulsion cosmetic further improved in stability of formulation in a system, wherein an ultraviolet scattering agent is contained, and a water-soluble alkyl-substituted polysaccharide derivative and any other emulsifying agent coexist.

Solution to Problem

In order to solve the above problem, the present inventors have earnestly studied, and as a result, found that by adjusting the content ratio between the water-soluble alkyl-substituted polysaccharide derivative and the emulsifying agent and the content ratio between the water-soluble alkyl-substituted polysaccharide derivative and the ultraviolet scattering agent to be in specific ranges, an oil-in-water emulsion cosmetic excellent in stability, particularly in stability given when the formulation is vibrated, while having high ultraviolet blocking capability can be obtained, and accordingly we have completed the present invention.

That is to say, the present invention provides an oil-in-water emulsion cosmetic comprising:
(A) a water-soluble alkyl-substituted polysaccharide derivative;
(B) a nonionic surfactant; and
(C) an ultraviolet scattering agent,
wherein a content ratio [(A)/(B)] of the water-soluble alkyl-substituted polysaccharide derivative (A) to the nonionic surfactant (B) is 1.54 or less, and a content ratio [(A)/(C)] of the water-soluble alkyl-substituted polysaccharide derivative (A) to the ultraviolet scattering agent (C) is 0.02 or less.

Advantageous Effects of Invention

The oil-in-water emulsion cosmetic of the present invention has high ultraviolet blocking capability (high protective capability against UV) and has high SPF and high PA. The oil-in-water emulsion cosmetic of the present invention is also excellent in texture and has been remarkably improved in stability. In particular, even if vibration is given, demulsification (emulsion breaking) does not take place in the cosmetic, so that the stability thereof can be maintained well. Moreover, although the cosmetic of the present invention is an oil-in-water emulsion cosmetic which is generally considered to have poor water resistance, the cosmetic exerts an unexpected effect, specifically, even when the cosmetic is washed off with water or warm water after applied onto the skin, the ultraviolet blocking effect therewith unaffectedly remains.

DESCRIPTION OF EMBODIMENTS

The present invention will be described in detail hereinafter.

The oil-in-water emulsion cosmetic of the present invention (hereinafter also simply referred to as an "emulsion cosmetic") comprises, as essential ingredients, (A) a water-soluble alkyl-substituted polysaccharide derivative, (B) a nonionic surfactant, and (C) an ultraviolet scattering agent.

The water-soluble alkyl-substituted polysaccharide derivative (A) in the present invention means one which has a polysaccharide or its derivative as a basic skeleton wherein a part or all of hydrogen atoms of the hydroxyl groups are substituted by glyceryl ether groups having a hydrophobic group, or sulfoalkyl groups or salts thereof, and which has water solubility (e.g., solubility in water at 25° C.: 0.001% by mass or more) (see Patent Document 4, etc.).

Examples of the polysaccharides or their derivatives each of which becomes a basic skeleton of the water-soluble alkyl-substituted polysaccharide derivative (A) include cellulose, guar gum, starch, hydroxyethyl cellulose, hydroxyethyl guar gum, hydroxyethyl starch, methylcellulose, methyl guar gum, methyl starch, ethyl cellulose, ethyl guar gum, ethyl starch, hydroxypropyl cellulose, hydroxypropyl guar gum, hydroxypropyl starch, hydroxyethyl methylcellulose, hydroxyethyl methyl guar gum, hydroxyethyl methyl starch, hydroxypropyl methylcellulose, hydroxypropyl methyl guar gum and hydroxypropyl methyl starch, and of these, preferable are cellulose, hydroxyethyl cellulose, methyl cellulose, ethyl cellulose and hydroxypropyl cellulose. The substituents of these polysaccharides, such as methyl group, ethyl group and hydroxyethyl group, may be those substituted by single substituents or may be those substituted by a plurality of substituents, and the degree of substitution per constituent monosaccharide residue is preferably 0.1 to 10, more preferably 0.5 to 5. The weight-average molecular weight of these polysaccharides or their derivatives is preferably 10000 to 10000000, more preferably 100000 to 5000000, still more preferably 300000 to 2000000.

The glyceryl ether group having a hydrophobic group is preferably selected from alkyl glyceryl ether groups having a straight-chain or branched alkyl group and alkenyl glyceryl, wherein each of the alkyl group and alkenyl group contains 10 to 40 carbon atoms, preferably 12 to 36 carbon atoms, more preferably 16 to 24 carbon atoms. Specific examples thereof include 2-hydroxy-3-alkoxypropyl group, 2-alkoxy-1-(hydroxymethyl)ethyl group, 2-hydroxy-3-alkenyloxypropyl group and 2-alkenyloxy-1-(hydroxymethyl)ethyl group, and these groups may be substituted for hydrogen atoms of hydroxyl groups of the hydroxyethyl groups or the hydroxypropyl groups bonded to the polysaccharide molecules.

The sulfoalkyl group or its salt is preferably a sulfoalkyl group having 1 to 5 carbon atoms which may be substituted by a hydroxyl group, or its salt. Specific examples of the sulfoalkyl groups include 2-sulfoethyl group, 3-sulfopropyl group, 3-sulfo-2-hydroxypropyl group and 2-sulfo-1-(hydroxymethyl)ethyl group, and all or a part of them may form salts together with alkali metals such as Na and K, alkaline earth metals such as Ca and Mg, organic cationic groups such as amines, ammonium ions, or the like.

Although the degree of substitution of the glyceryl ether group having a hydrophobic group in the water-soluble alkyl-substituted polysaccharide derivative is not particularly limited, it is preferably 0.001 to 1, more preferably 0.002 to 0.5, still more preferably 0.003 to 0.1, per constituent monosaccharide residue.

Examples of the water-soluble alkyl-substituted polysaccharide derivatives (A) used in the present invention include those having cellulose as a basic skeleton, that is, hydrophobically modified alkyl celluloses, specifically alkyl celluloses hydrophobically modified with an alkyl group having 14 to 22 carbon atoms, preferably 14 to 20 carbon atoms, e.g., those represented by the following general formula (I).

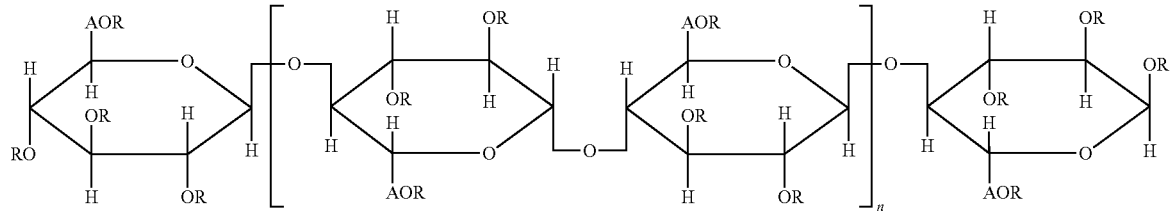

(I)

In the formula, R may be the same or different, represents one or more groups selected from a hydrogen atom, an alkyl group having 1 to 4 carbon atoms, a group —[$CH_2CH(CH_3)O$]$_m$—H (wherein m is an integer of 1 to 5, preferably 1 to 3), a group —$CH_2CH_2OH$, and a group —$CH_2CH(OH)CH_2OR'$ (wherein R' is an alkyl group having 14 to 22 carbon atoms), and mandatorily contain a group —$CH_2CH(OH)CH_2OR'$. A is a group —$(CH_2)_q$— (q is an integer of 1 to 3, preferably 1), and n is an integer of 100 to 10000, preferably 500 to 5000.

The hydrophobically modified alkyl cellulose of the formula (I) can be obtained by a production process basically including bringing a long-chain alkyl group introducing compound having 14 to 22 carbon atoms, such as a long-chain alkyl glycidyl ether of the following formula (II), into contact with a water-soluble cellulose ether derivative that becomes a basic skeleton, such as methyl cellulose (R in the formula (I) is a hydrogen atom or a methyl group), ethyl cellulose (R in the formula (I) is a hydrogen atom or an ethyl group), propyl cellulose (R in the formula (I) is a hydrogen atom or a propyl group), butyl cellulose (R in the formula (1)

is a hydrogen atom or a butyl group), hydroxypropyl cellulose [R in the formula (I) is a hydrogen atom or a hydroxypropyl group ($-[CH_2CH(CH_3)O]_m-H$ (wherein m is an integer of 1 to 5, preferably 1 to 3))], or hydroxypropyl methyl cellulose (R in the formula (I) is a hydrogen atom, a methyl group or a hydroxypropyl group), in the presence of an alkali catalyst.

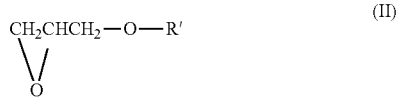
(II)

wherein R' is an alkyl group having 14 to 22 carbon atoms.

The content of the group $-CH_2CH(OH)CH_2OR'$ introduced into the hydrophobically modified alkyl cellulose is preferably about 0.1 to 5.0% by mass based on the whole of the hydrophobically modified alkyl cellulose. For obtaining such a content, the molar ratio between the water-soluble cellulose ether derivative and the long-chain alkyl glycidyl ether in the reaction, the reaction time, the of the alkali catalyst, etc. only need to be appropriately selected to produce the hydrophobically modified alkyl cellulose. After the above reaction, purification steps, such as neutralization, filtration, washing, drying and sifting of the reaction product, may be carried out.

The weight-average molecular weight of the hydrophobically modified alkyl cellulose is preferably 100000 to 1000000, more preferably 300000 to 800000, still more preferably 550000 to 750000.

Of the above water-soluble cellulose ether derivatives, a particularly preferred example is Hydroxypropylmethylcellulose Stearoxy Ether which has hydroxypropyl methyl cellulose as a basic skeleton and in which R' in the long-chain alkyl glycidyl ether introduced is a stearyl group having 18 carbon atoms ($-C_{18}H_{37}$).

As the hydrophobically modified alkyl cellulose, a commercial product can also be used, and examples thereof include Sangelose 90L (labeling name: Hydrophobic Hydroxypropyl Methylcellulose, manufactured by Daido Chemical Corporation), Natrosol® Plus 330 cs (manufactured by Ashland), and Polysurf® 67 cs (manufactured by Ashland).

The content of the water-soluble alkyl-substituted polysaccharide derivative (A) in the emulsion cosmetic of the present invention is 0.01 to 3% by mass, preferably 0.01 to 1% by mass, more preferably 0.01 to 0.2% by mass. If the content is less than 0.01% by mass, the effects of the present invention, such as stabilization, cannot be obtained. The upper limit of the content only needs to be 3% by mass or less, and may be set to less than 0.2% by mass, e.g., 0.1% by mass, 0.08% by mass, 0.05% by mass or 0.04% by mass.

The nonionic surfactant (B) used in the emulsion cosmetic of the present invention only needs to be a nonionic surfactant capable of being contained in cosmetics, and can be selected from nonionic surfactants of polyhydric alcohol ester, such as fatty acid glycerides, propylene glycol fatty acid esters and sorbitan fatty acid esters, and nonionic surfactants of oxyalkylene condensation, such as higher alcohol alkylene oxide condensates, fatty acid alkylene oxide condensates, oxyalkylene condensates of sorbitan fatty acid esters and a polyoxyethylene/polyoxypropylene block copolymer.

In the present invention, it is preferable to use a nonionic surfactant having an HLB value of 9 or more, preferably 10 or more, more preferably 12 or more. Specific examples thereof include, but not limited to, polyoxyalkylene glyceryl fatty acid esters, such as PEG-60 glyceryl isostearate, polyoxyalkylene hydrogenated castor oils, such as PEG-100 Hydrogenated Castor Oil and PEG-60 Hydrogenated Castor Oil, glyceryl fatty acid esters, such as glyceryl cocoate and glyceryl laurate, and sorbitan fatty acid esters, such as sorbitan palmitate and sorbitan cocoate.

The content of the nonionic surfactant (B) in the emulsion cosmetic of the present invention is 0.1 to 5% by mass, preferably 0.5 to 3% by mass, more preferably 1 to 2% by mass. If the content is less than 0.1% by mass, the emulsion stability tends to decrease, and if more than 5% by mass of the nonionic surfactant (B) is contained, the feeling of use is sticky and water resistance sometimes decreases.

The ultraviolet scattering agent (C) to be contained in the emulsion cosmetic of the present invention can be appropriately selected from ultraviolet scattering agents usually used in cosmetics, without particular restriction. Specific examples thereof include titanium dioxide, zinc oxide, silica, and composite powders, such as titanium dioxide coated mica, titanium dioxide coated bismuth oxychloride, titanium dioxide coated talc and titanium dioxide coated glass flake. In particular, micro particle zinc oxide and micro particle titanium dioxide having an average particle diameter of about 25 to 100 nm are preferable.

The ultraviolet scattering agent (C) in the present invention preferably has a hydrophobic surface obtained by hydrophobically treating a surface of a base material such as zinc oxide or titanium dioxide. Examples of methods of hydrophobic treatment of surface include silicone treatment using methylhydrogen polysiloxane, methyl polysiloxane, trimethylsiloxysilicic acid, silicone resin or the like; fluorine treatment using perfluoroalkyl phosphoric acid ester, perfluoroalcohol or the like; amino acid treatment using N-acylglutamic acid or the like; lecithin treatment; metallic soap treatment; fatty acid treatment; and alkylphosphoric acid ester treatment.

The content of the ultraviolet scattering agent (C) in the emulsion cosmetic of the present invention is 2.5 to 30% by mass, preferably 3 to 25% by mass, more preferably 4 to 20% by mass. If the content is less than 2.5% by mass, it is difficult to obtain a high SPF value, and if more than 30% by mass of the ultraviolet scattering agent (C) is contained, emulsion stability and texture sometimes decrease.

The emulsion cosmetic of the present invention is characterized in that the stability has been improved by adjusting the content ratio [(A)/(B)] of the water-soluble alkyl-substituted polysaccharide derivative (A) to the nonionic surfactant (B) and the content ratio [(A)/(C)] of the water-soluble alkyl-substituted polysaccharide derivative (A) to the ultraviolet scattering agent (C) to be in the specific ranges.

The content ratio [(A)/(B)] of the water-soluble alkyl-substituted polysaccharide derivative (A) to the nonionic surfactant (B) is adjusted to 1.54 or less, preferably 1.50 or less, more preferably 1.0 or less, still more preferably 0.5 or less. The lower limit of this ratio is not particularly limited, and it is usually not less than 0.001.

The content ratio [(A)/(C)] of the water-soluble alkyl-substituted polysaccharide derivative (A) to the ultraviolet scattering agent (C) is adjusted to 0.02 or less, preferably 0.015 or less, more preferably 0.01 or less. The lower limit of this ratio is not particularly limited, and it is usually not less than 0.002.

It has been confirmed that when a hydrogenated castor oil alkylene oxide condensate (hereinafter also referred to as a "hydrogenated castor oil-based nonionic surfactant") is selected as the nonionic surfactant (B) in the present invention, a desired effect (improvement in stability) is obtained even if the content ratio [(A)/(B)] of the water-soluble alkyl-substituted polysaccharide derivative (A) to the nonionic surfactant (B) and the content ratio [(A)/(C)] of the water-soluble alkyl-substituted polysaccharide derivative (A) to the ultraviolet scattering agent (C) are not adjusted to be in the above ranges.

Accordingly, the present invention provides, as another aspect, an oil-in-water emulsion cosmetic comprising (A) a water-soluble alkyl-substituted polysaccharide derivative, (B) a hydrogenated castor oil-based nonionic surfactant, and (C) an ultraviolet scattering agent.

The hydrogenated castor oil-based nonionic surfactant (B) in this aspect is also preferably selected from hydrogenated castor oil-based nonionic surfactants having an HLB value of 9 or more, preferably 10 or more, more preferably 12 or more. Specific examples thereof include, but not limited to, PEG-200 hydrogenated castor oil, PEG-100 hydrogenated castor oil, PEG-60 hydrogenated castor oil, PEG-80 hydrogenated castor oil, PEG-55 hydrogenated castor oil, PEG-50 hydrogenated castor oil, PEG-40 hydrogenated castor oil, PEG-35 hydrogenated castor oil, PEG-30 hydrogenated castor oil, PEG-25 hydrogenated castor oil, PEG-20 hydrogenated castor oil, PEG-60 hydrogenated castor oil isostearate, PEG-50 hydrogenated castor oil isostearate, PEG-40 hydrogenated castor oil isostearate, PEG-30 hydrogenated castor oil isostearate, PEG-60 hydrogenated castor oil laurate, PEG-50 hydrogenated castor oil laurate, PEG-40 hydrogenated castor oil laurate, PEG-30 hydrogenated castor oil laurate, PEG-30 hydrogenated castor oil PCA isostearate, PEG-40 hydrogenated castor oil PCA isostearate, PEG-60 hydrogenated castor oil PCA isostearate, PEG-50 hydrogenated castor oil succinate, PEG-60 hydrogenated castor oil triisostearate, and PEG-50 hydrogenated castor oil triisostearate.

Also, in this aspect, the contents of the water-soluble alkyl-substituted polysaccharide derivative (A), the hydrogenated castor oil-based nonionic surfactant (B) and the ultraviolet scattering agent (C) are preferably in the aforesaid preferred ranges.

The cosmetic of the present invention is an oil-in-water emulsion cosmetic, and contains a water phase as an external phase (continuous phase) and an oil phase as an internal phase (dispersed phase).

In the case where the emulsion cosmetic of the present invention is used as a sunscreen cosmetic, by containing a water-soluble or oil-soluble ultraviolet absorber in the oil phase or the water phase, this ultraviolet absorber and the aforesaid ultraviolet scattering agent (C) work together and exert good ultraviolet blocking capability in a wide wavelength range of UVA region to UVB region, thereby achieving high SPF and high PA. From the viewpoint of stability, it is preferable to particularly contain an oil-soluble ultraviolet absorber in the oil phase.

Examples of the oil-soluble ultraviolet absorbers used in the present invention include benzoic acid derivatives, salicylic acid derivatives, cinnamic acid derivatives, dibenzoylmethane derivatives, β,β-diphenyl acrylate derivatives, benzophenone derivatives, benzylidene camphor derivatives, phenylbenzimidazole derivatives, triazine derivatives, phenylbenzotriazole derivatives, anthranil derivatives, imidazoline derivatives, benzal malonate derivatives, and 4,4-diarylbutadiene derivatives. Specific examples, trade names (as example), etc. are enumerated below, but the oil-soluble ultraviolet absorbers are not limited thereto.

Examples of the benzoic acid derivatives include ethyl p-aminobenzoate (PABA), ethyl dihydroxypropyl PABA, ethylhexyl dimethyl PABA (e.g., "Escalol® 507; ISP), glyceryl PABA, PEG-25 PABA (e.g., "Uvinul® P25"; BASF), and diethylamino hydroxybenzoyl hexyl benzoate (e.g., "Uvinul® A Plus").

Examples of the salicylic acid derivatives include homosalate ("Eusolex® HMS"; Rona/EM Industries, Inc.), ethylhexyl salicylate (e.g., "Neo Heliopan® OS"; Haarmann & Reimer), dipropylene glycol salicylate (e.g., "Dipsal®"; Scher), and TEA-salicylate (e.g., "Neo Heliopan® TS"; Haarmann & Reimer).

Examples of the cinnamic acid derivatives include octyl methoxycinnamate or ethylhexyl methoxycinnamate (e.g., "Parsol® MCX"; Hoffmann-La Roche, Ltd.), isopropyl methoxycinnamate, isoamyl methoxycinnamate (e.g., "Neo Heliopan® E1000"; Haarmann & Reimer), cinoxate, DEA methoxycinnamate, diisopropyl methylcinnamate, glyceryl ethylhexanoate dimethoxycinnamate, and di-(2-ethylhexyl)-4'-methoxybenzal malonate.

Examples of the dibenzoylmethane derivatives include 4-tert-butyl-4'-methoxydibenzoylmethane (e.g., "Parsol® 1789").

Examples of the β,β-diphenyl acrylate derivatives include octocrylene (e.g., Uvinul® N539"; BASF).

Examples of the benzophenone derivatives include benzophenone-1 (e.g., "Uvinul® 400"; BASF), benzophenone-2 (e.g., "Uvinul® D50"; BASF), benzophenone-3 or oxybenzone (e.g., "Uvinul® M40"; BASF), benzophenone-4 (e.g., "Uvinul® MS40"; BASF), benzophenone-5, benzophenone-6 (e.g., "Helisorb® 11"; Norquay Technology Inc.), benzophenone-8 (e.g., "Spectra-Sorb® UV-24"; American Cyanamid Co.), benzophenone-9 (e.g., "Uvinul® DS-49"; BASF), and benzophenone-12.

Examples of the benzylidene camphor derivatives include 3-benzylidene camphor (e.g., "Mexoryl® SD"; Chimex), 4-methylbenzylidene camphor, benzylidene camphor sulfonic acid (e.g., "Mexoryl® SL"; Chimex), camphor benzalkonium methosulfate (e.g., "Mexoryl® SO"; Chimex), terephthalylidene dicamphor sulfonic acid (e.g., "Mexoryl® SX"; Chimex), and polyacrylamide methylbenzylidene camphor (e.g., "Mexoryl® SW"; Chimex).

Examples of the phenylbenzimidazole derivatives include phenylbenzimidazole sulfonic acid (e.g., "Eusolex® 232"; Merck KGaA), and disodium phenyl dibenzimidazole tetrasulfonate (e.g., "Neo Heliopan® AP"; Haarmann & Reimer).

Examples of the triazine derivatives include anisotriazine (e.g., "Tinosorb® S"; Ciba Specialty Chemicals Inc.), ethylhexyl triazone (e.g., "Uvinul® T-150"; BASF), diethylhexyl butamido triazone (e.g., "Uvasorb® HEB"; 3V SIGMA S.p.A.), and 2,4,6-tris(diisobutyl-4'-aminobenzalmalonate)-s-triazine.

Examples of the phenylbenzotriazole derivatives include drometrizole trisiloxane (e.g., "Silatrizole®"; Rhodia Chimie), and methylene bis-benzotriazolyl tetramethylbutylphenol (e.g., "Tinosorb® M"; Ciba Specialty Chemicals Inc.).

Examples of the anthanil derivatives include menthyl anthranilate (e.g., "Neo Heliopan® MA"; Haarmann & Reimer).

Examples of the imidazoline derivatives include ethyihexyl dimethoxybenzylidene dioxoimidazoline propionate.

Examples of the benzal malonate derivatives include polyorganosiloxane having a benzal malonate functional group (e.g., Polysilicone-15; "Parsol® SLX"; DSM Nutrition Japan K.K.).

Examples of the 4,4-diarylbutadiene derivatives include 1,1-dicarboxy(2,2'-dimethylpropyl)-4,4-diphenylbutadiene.

The content of the ultraviolet absorber based on the whole emulsion cosmetic is not particularly limited, and it is usually 1 to 25% by mass, preferably 3 to 20% by mass, more preferably 5 to 18% by mass.

In addition to the above-described essential ingredients (A) to (C) and ultraviolet absorber, various ingredients usually contained in cosmetics can be contained in the emulsion cosmetic of the present invention within limits not detrimental to the effects of the present invention. Specific examples thereof include, but not limited to, liquid, solid or semisolid oils (including hydrocarbon oil, ester oil, oils and fats, higher alcohol, higher fatty acid and silicone oil, and including volatile and nonvolatile oils), moisturizers, thickening agents, such as water-soluble polymers, lower alcohols having 1 to 6 carbon atoms, pH adjustors, chelating agents, antioxidants, and various medicines.

Examples of the moisturizers include glycols, such as propylene glycol, dipropylene glycol, 1,3-butylene glycol, 1,4-butylene glycol, diethylene glycol, triethylene glycol and polyethylene glycol; glycerins, such as glycerin, diglycerin and polyglycerin; sugar alcohols, such as sorbitol, mannitol, maltitol, xylitol and erythritol; and saccharides, such as fructose, glucose, galactose, maltose, lactose and trehalose.

Examples of the thickening agents (water-soluble polymers) include plant-based polymers, such as gum arabic, gum tragacanth, galactan, guar gum, carob gum, karaya gum, gellan gum and carrageenan; microbial polymers, such as xanthan gum, dextran, succinoglucan and pullulan; animal-based polymers, such as collagen, casein, albumin and gelatin; starch-based polymers, such as carboxymethyl starch and methyl hydroxypropyl starch; and alginic acid-based polymers, such as sodium alginate and propylene glycol alginate.

Examples of various medicines include vitamins, such as magnesium ascorbyl phosphate, ascorbic acid glucoside, vitamin B6 hydrochloride and pantothenyl ethyl ether; whitening agent such as tranexamic acid, bactericide, anti-inflammatory agent, antiseptic agent, plant extract, amino acid, and refreshing agent.

The emulsion cosmetic of the present invention can be prepared in accordance with a method usually used for oil-in-water emulsion cosmetics. That is to say, the emulsion cosmetic can be prepared by separately mixing the water phase ingredients and the oil phase ingredients, adding the oil phase ingredients to the water phase ingredients while stirring the water phase ingredients, and emulsifying them.

The oil-in-water emulsion cosmetic of the present invention can be provided as a skincare, makeup or hair cosmetic particularly having an excellent ultraviolet blocking effect. The emulsion cosmetic of the present invention can be provided in a product form of lotion, cream, milky lotion, gel, mousse, spray or mist having a fresh feeling of use. The emulsion cosmetic of the present invention is capable to maintain the emulsion stability even if it is vibrated, and therefore, the emulsion cosmetic is suitable also to be applied to a portable cosmetic. Moreover, the ultraviolet blocking effect lasts even if the emulsion cosmetic is washed off with water or warm water, and therefore, the emulsion cosmetic can be provided for a wash-off product.

EXAMPLES

The present invention will be described in more detail with reference to the following specific examples, but the technical scope of the present invention is in no way limited to those examples. Unless otherwise noted, the contents in the following examples, etc. are expressed in % by mass.

Oil-in-water emulsion cosmetics were prepared according to the formulations shown in Table 1 described below, and vibration stability and texture were evaluated in the following manner.

Evaluation of Vibration Stability

A closed container was filled with the cosmetic (sample) of each example and vibrated at a rate of 2500 rpm for 30 minutes at 37° C., and the state of each cosmetic was evaluated by visual observation and an actual use test.

Evaluation Result

A: Unchanged

B: The cosmetic suffered occurrence of demulsification due to vibrations and was incapable of being used as a product.

Evaluation of Texture

The cosmetic (sample) of each example was evaluated through an actual use test by a panel of experts.

Evaluation Result

A: Fresh

B: The cosmetic has heavy spreadability, so that it cannot be easily and evenly spread.

TABLE 1

|  |  | Example 1 | Example 2 | Comparative Example 1 | Comparative Example 2 | Example 3 | Example 4 | Example 5 |
|---|---|---|---|---|---|---|---|---|
| Water | Water | balance | balance | balance | balance | balance | balance | balance |
| Moisturizer | Butylene Glycol | 7 | 7 | 7 | 7 | 7 | 7 | 7 |
|  | Glycerin | 3 | 3 | 3 | 3 | 3 | 3 | 3 |
| Thickening agent | (Dimethylacrylamide/Sodium Acryloyldimethyl Taurate) Crosspolymer | 1 | 1 | 1 | 1 | 1 | 1 | 1 |
|  | Hydroxypropylmethylcellulose Stearoxy Ether | 0.04 | 0.04 | 0.2 | 0.6 | 0.1 | 0.04 | 0.04 |
| Active agent | PEG-100 Hydrogenated Castor Oil | 0.2 | — | — | — | 0.2 | 0.1 | 1 |
| PEG-60 | Hydrogenated Castor Oil | 1.3 | — | — | — | 1.3 | 0.8 | 2.2 |
|  | PEG-60 Glyceryl Isostearate | — | 1.5 | 0.1 | 1.5 | — | — | — |
|  | Sorbitan Sesquiisostearate | 0.5 | 0.5 | — | 0.5 | 0.5 | 0.1 | 0.8 |
| Oil | Cyclomethicone | 20 | 20 | 20 | 20 | 20 | 7 | 20 |
|  | Isostearic Acid | 1 | 1 | 1 | 1 | 1 | 1 | 1 |
|  | EthylhexylTriazone | 1 | 1 | 1 | 1 | 1 | 1 | 1 |
|  | Ethylhexyl Methoxycinnamate | 7 | 7 | 7 | 7 | 7 | 7 | 7 |
|  | Bis-Ethylhexyloxyphenol | 2 | 2 | 2 | 2 | 2 | 2 | 2 |

TABLE 1-continued

|  |  | Example 1 | Example 2 | Comparative Example 1 | Comparative Example 2 | Example 3 | Example 4 | Example 5 |
|---|---|---|---|---|---|---|---|---|
|  | Methoxyphenyl Triazine |  |  |  |  |  |  |  |
|  | PPG-17 | 1 | 1 | 1 | 1 | 1 | 1 | 1 |
|  | Dimethicone | 5 | 5 | 5 | 5 | 5 | 5 | 5 |
| Scattering agent | Hydrophobically Treated Zinc Oxide | 14 | 14 | 14 | 14 | 14 | 4 | 14 |
| Chelating agent | EDTA-2Na | q.s. | q.s. | q.s. | q.s. | q.s. | q.s. | q.s. |
| Whitening agent | Tranexamic Acid | 2 | 2 | 2 | 2 | 2 | 2 | 2 |
| Alcohol | Ethanol | 5 | 5 | 5 | 5 | 5 | 5 | 5 |
| Antiseptic agent | Phenoxyethanol | q.s. | q.s. | q.s. | q.s. | q.s. | q.s. | q.s. |
|  | Total | 100 | 100 | 100 | 100 | 100 | 100 | 100 |
|  | (A)/(B) | 0.02 | 0.02 | 2.0 | 0.3 | 0.05 | 0.04 | 0.01 |
|  | (A)/(C) | 0.0029 | 0.0029 | 0.0143 | 0.0429 | 0.0071 | 0.0100 | 0.0029 |
|  | Vibration stability | A | A | B | B | A | A | A |
|  | Texture | A | A | B | B | A | A | A |

As shown in Table 1, Examples 1 to 5 each satisfying the conditions of the present invention that the content ratio [(A)/(B)] of the water-soluble alkyl-substituted polysaccharide derivative (A) to the nonionic surfactant (B) is 1.54 or less and the content ratio [(A)/(C)] of the water-soluble alkyl-substituted polysaccharide derivative (A) to the ultraviolet scattering agent (C) is 0.02 or less maintained emulsion stability in the severe vibration test and were excellent also in texture even though any of a hydrogenated castor oil-based nonionic surfactant and an another nonionic surfactant was used as the nonionic surfactant (B). However, Comparative Example 1 having [(A)/(B)] of more than 1.54 and Comparative Example 2 having [(A)/(C)] of more than 0.02 failed to maintain emulsion stability after the vibration test, and also had poor texture.

Next, sunscreen cosmetics were prepared according to the formulations shown in Tables 2 to 5 described below. The cosmetic (sample) of each example was applied to faces of subjects (a panel of experts) and washed off with water, and then the following properties were evaluated. The evaluation results are set forth in Table 6.

Persistence of UV Blocking Effect

The faces of the subjects were photographed by a commercial UV camera, and from the resulting images, a luminance ("luminance of bare skin") of a cheek portion was calculated.

Subsequently, the cosmetic (sample) of each example was applied to the faces of the subjects, rinsed with water and then dried off with a towel, and similarly, the faces of the subjects were photographed by a commercial UV camera, and from the resulting images, a luminance ("luminance after application/washing with water") of a cheek portion was calculated.

A value of (luminance of bare skin)−(luminance after application/washing with water) was taken as an indication of "persistence of UV blocking effect". It is thought that as this value increases, the UV blocking effect remains higher.

Bare Skin Feeling After Washing Off

The feeling after the cosmetic (sample) of each example was washed off in the above test was evaluated based on the following criteria.

Evaluation Results

A: A feeling like bare skin onto which nothing is applied.

B: A feeling such that more or less cosmetic remains on the skin.

C: A feeling such that cosmetic remains on the skin.

TABLE 2

| Ingredient | Comparative Example 3 |
|---|---|
| Purified Water | Balance |
| Octocrylene | 5 |
| Diethylamino Hydroxybenzoyl Hexyl Benzoate | 2 |
| 2,4-Bis4[[4-(2-ethylhexyloxy)-2-hydroxy] phenyl]-6-(4-methoxyphenyl)-1,3,5-triazine | 1 |
| Dextrin Palmitate | 1 |
| Cetyl 2-Ethylhexanoate | 4 |
| Glyceryl Tri-2-Ethylhexanoate | 4 |
| Diisopropyl Sebacate | 7 |
| Dimethylpolysiloxane (*1) | 2 |
| Decamethylcyclopentasiloxane | 25 |
| Lauryl PEG-9 Polydimethylsiloxyethyl Dimethicone | 1 |
| Decamethyltetrasiloxane | 10 |
| Dimethyldistearyl Ammonium Hectorite | 0.5 |
| Ethanol (*2) | 8 |
| Glycerin | 1 |
| Trisodium Edetate | q.s. |
| Perfume | q.s. |
| Table Salt | q.s. |
| Talc | 5 |
| Total | 100 |

(*1) KE-96A-6T (manufactured by Shin-Etsu Chemical Co., Ltd.)
(*2) Synthetic alcohol, alcohol content of 95% (manufactured by Japan Alcohol Trading Co., Ltd.)

Production Method:

The oil phase ingredients were mixed, the powder was dispersed, and then the water phase ingredients were added, followed by carrying out emulsification treatment.

TABLE 3

| Ingredient name | Comparative Example 4 |
|---|---|
| Purified Water | balance |
| Titanium Dioxide | 5 |
| Homosalate | 5 |
| Octocrylene | 5 |
| Octyl Salicylate | 5 |
| Sodium Laureth Sulfate Na | 10 |
| Cocamidopropyl Betaine | 10 |
| Polyethylene Glycol Monostearate | 5 |
| Glyceryl Stearate | 3 |
| EDTA-2Na | q.s. |
| Xanthan Gum | q.s. |
| Perfume | q.s. |

TABLE 3-continued

| Ingredient name | Comparative Example 4 |
|---|---|
| Total | 100 |

Production Method:

Purified water was warmed, the active agent was mixed and stirred, and then the oil phase was added to be stirred and mixed, followed by carrying out cooling.

TABLE 4

| Ingredient name | Comparative Example 5 |
|---|---|
| Shea Butter | 60 |
| Zinc Oxide | 10 |
| Octocrylene | 5 |
| Ethylhexyl Methoxycinnamate | 5 |
| Olive Oil | 19 |
| Perfume | q.s. |
| Total | 100 |

Production Method:

The oil phase was warmed, and the powder was dispersed, followed by carrying out cooling to solidify.

TABLE 5

| Ingredient | Example 6 |
|---|---|
| Water | balance |
| Butylene Glycol | 7 |
| Glycerin | 3 |
| (Dimethylacrylamide/Sodium Acryloyldimethyl Taurate) Crosspolymer | 1 |
| Hydroxypropylmethylcellulose Stearoxy Ether | 0.04 |
| PEG-60 Hydrogenated Castor Oil | 1.3 |
| Cyclomethicone | 20 |
| Isostearic Acid | 1 |
| Sorbitan Sesquiisostearate | 0.5 |
| Ethylhexyl Triazone | 1 |
| Ethylhexyl Methoxycinnamate | 7 |
| Bis-Ethylhexyloxyphenol Methoxyphenyl Triazine | 2 |
| PPG-17 | 1 |
| Dimethicone | 3 |
| Zinc Oxide | 10 |
| EDTA-2Na | q.s. |
| Ethanol | 5 |
| Phenoxyethanol | q.s. |
| Total | 100 |

Production Method:

The water phase ingredients were mixed, and the oil phase ingredients in which the powder had been dispersed were added, followed by carrying out emulsification treatment.

TABLE 6

| | Comparative Example 3 | Comparative Example 4 | Comparative Example 5 | Example 6 |
|---|---|---|---|---|
| Persistence of UV blocking effect | 95.4 | 51.8 | 88.6 | 87.8 |
| Bare skin feeling after washing off | B | A | C | A |

In Comparative Example 3 which was an oil-in-water emulsion cosmetic containing no ultraviolet scattering agent such as Zinc Oxide or Titanium Dioxide and in which an oily ultraviolet absorber had UV blocking capability, the oily ultraviolet absorber remained even though the cosmetic was washed off with water, and the UV blocking capability was maintained, but there was a film feeling considered to be attributable to the oily thickening agent, etc. having been contained in order to improve emulsion stability and the like. Comparative Example 4 which was an oil-in-water emulsion cosmetic in which Titanium Dioxide had been contained did not contain any water-soluble alkyl-substituted polysaccharide derivative, and therefore, by washing off the cosmetic with water, the ultraviolet scattering agent run off, and the UV blocking effect was unable to be maintained.

Comparative Example 5 which was an oily cosmetic containing an ultraviolet scattering agent (Zinc Oxide) but not containing water left an oil film even though the cosmetic was washed off with water, and therefore, run-off of the ultraviolet scattering agent was suppressed, but even after the cosmetic was washed off, there was an oily feeling that was far from a bare skin feeling. In contrast with them, Example 6 which was the oil-in-water emulsion cosmetic of the present invention maintained an UV blocking effect at the same level as that of an oily cosmetic even though the emulsion cosmetic was washed off with water, and after the emulsion cosmetic was washed off, there was a feeling like bare skin onto which nothing had been applied.

Other formulation examples of the emulsion cosmetics of the present invention will be described below.

| Formulation Example 1: foam aerosol sunscreen | |
|---|---|
| Ingredient name | Content |
| Purified water | balance |
| Ethanol | 5 |
| Citric Acid | q.s. |
| Sodium Citrate | q.s. |
| Sodium Hyaluronate | 0.1 |
| Black Tea Extract | 0.1 |
| Bentonite | 1 |
| Talc | 3 |
| Micro Particle Titanium Dioxide | 3 |
| (Acrylates/Alkyl Acrylate(C10-30)) Crosspolymer | 0.1 |
| Hydroxypropylmethylcellulose Stearoxy Ether | 0.04 |
| Polyoxyethylene Hydrogenated Castor Oil (60 mol) | 2 |
| Glycerin | 1 |
| Butylene Glycol | 1 |
| Triethanolamine | 0.1 |
| Ethylhexyl Methoxycinnamate | 10 |
| Diethylamino Hydroxybenzoyl Hexyl Benzoate | 2 |
| Bis-Ethylhexyloxyphenol Methoxyphenyl Triazine | 2 |
| Ethylhexyl Salicylate | 3 |
| Diisopropyl Sebacate | 3 |
| Polypropylene Glycol (17) | 1 |
| Dimethicone (6 cs) | 3 |
| Dextrin (Palmitate/Ethylhexanoate) | 1 |
| Lauryl Dimethylaminoacetic Acid Betaine 35% Aqueous Solution | 0.2 |
| PEG-10 Dimethicone | 0.01 |
| Menthol | 0.3 |
| Tocopherol | q.s. |
| Perfume | q.s. |
| Total | 100 |

A container was filled with 90% of a stock solution of the above formulation and 10% of a propellant (LPG), thereby preparing a foam sunscreen product.

Formulation Example 2: gel-like BB cream

| Ingredient name | Content |
| --- | --- |
| Purified Water | balance |
| Ethanol | 10 |
| Sodium Hyaluronate | 0.1 |
| Hestnut Rose Extract | 0.1 |
| Hydroxypropylmethylcellulose Stearoxy Ether | 0.15 |
| (Dimethylacrylamide/Sodium Acryloyldimethyl Taurate) Copolymer | 0.2 |
| Succinoglucan | 0.1 |
| Polyoxyethylene (8 mol) Behenyl Ether | 0.15 |
| Glycerin | 3 |
| Polyethylene Glycol (molecular weight 300) | 5 |
| Bis-PEG-18 Methyl Ether Dimethyl Silane | 3 |
| Polyoxyethylene (14) Polyoxypropylene (7) Dimethyl Ether | 1 |
| Ethylhexyl Methoxycinnamate | 10 |
| Diethylamino Hydroxybenzoyl Hexyl Benzoate | 1 |
| Bis-Ethylhexyloxyphenol Methoxyphenyl Triazine | 3 |
| Hydrogen Dimethicone/Aluminum Hydroxide Treated Micro Particle Titanium Dioxide | 8 |
| Octyltriethoxysilane Treated Micro Particle Zinc Oxide (particle diameter 25 nm) | 3 |
| Octyltriethoxysilane Treated Pigmentary Titanium | 4 |
| Octyltriethoxysilane Treated Red Iron Oxide | q.s. |
| Octyltriethoxysilane Treated Yellow Iron Oxide | q.s. |
| Octyltriethoxysilane Treated Black Iron Oxide | q.s. |
| Caprylyl Methicone | 2 |
| Polypropylene Glycol (17) | 2 |
| Di(Cholesteryl/Phytosteryl) N-Lauroyl-L-Glutamate | 0.5 |
| Dextrin (Palmitate/Ethylhexanoate) | 0.5 |
| Perfume | q.s. |
| Silica | 1 |
| Total | 100 |

Formulation Example 3: BB cream

| Ingredient name | Content |
| --- | --- |
| Purified Water | balance |
| Ethanol | 8 |
| EDTA-2Na•H$_2$0 | q.s. |
| Sodium Hexametaphosphate | q.s. |
| Citric Acid | q.s. |
| Sodium Citrate | q.s. |
| Magnesium L-Ascorbyl-2-phosphate | 0.5 |
| Sodium Acetylated Hyaluronate | 0.1 |
| Water-soluble Collagen | 0.1 |
| Hestnut Rose Extract | 0.1 |
| (Dimethylacrylamide/Sodium Acryloyldimethyl Taurate) Copolymer | 0.3 |
| Succinoglucan | 0.2 |
| Cellulose Gum | 0.2 |
| Hydroxypropylmethylcellulose Stearoxy Ether | 0.04 |
| Glycerin | 2 |
| Butylene Glycol | 5 |
| Polyoxyethylene (14) Polyoxypropylene (7) Dimethyl Ether | 1 |
| Polyoxyethylene Hydrogenated Castor Oil (100 mol) | 1 |
| Polyoxyethylene (8 mol) Behenyl Ether | 1 |
| Sodium Methyl Stearoyl Taurate | 0.1 |
| Stearyl Alcohol | 0.5 |
| Behenyl Alcohol | 0.5 |
| Ethylhexyl Methoxycinnamate | 10 |
| Ethylhexyl Triazine | 1 |
| Diethylamino Hydroxybenzoyl Hexyl Benzoate | 1 |
| Bis-Ethylhexyloxyphenol Methoxyphenyl Triazine | 1 |
| Isododecane | 10 |
| Caprylyl Methicone | 5 |
| Dimethicone (6 cs) | 5 |
| Phytosteryl Macadamiate | 1 |
| Di(Phytosteryl/Octyldodecyl) N-Lauroyl-L-Glutamate | 0.5 |
| Dextrin (Palmitate/Ethylhexanoate) | 0.5 |
| Octyltriethoxysilane Treated Micro Particle Zinc Oxide (particle diameter 25 nm) | 8 |
| Alumina Treated Pigmentary Titanium Dioxide | 4 |
| Octyltriethoxysilane Treated Red Iron Oxide | q.s. |
| Octyltriethoxysilane Treated Yellow Iron Oxide | q.s. |
| Octyltriethoxysilane Treated Black Iron Oxide | q.s. |
| Isotearic Acid | 0.5 |
| Sorbitan Sesquisostearate | 0.5 |
| Perfume | q.s. |
| Talc | 3 |
| Silica | 3 |
| Starch Powder | 1 |
| Total | 100 |

The invention claimed is:

1. An oil-in-water emulsion cosmetic, comprising:
   (A) a water-soluble alkyl-substituted polysaccharide derivative;
   (B) a nonionic surfactant; and
   (C) an ultraviolet scattering agent;
   wherein a content ratio [(A)/(B)] of said water-soluble alkyl-substituted polysaccharide derivative (A) to said nonionic surfactant (B) is not larger than 1.54; and
   wherein a content ratio [(A)/(C)] of said water-soluble alkyl-substituted polysaccharide derivative (A) to said ultraviolet scattering agent (C) is not larger than 0.01.

2. The cosmetic, according to claim 1, wherein:
   a content of said water-soluble alkyl-substituted polysaccharide derivative (A) is 0.01 to 3% by mass;
   a content of said nonionic surfactant (B) is 0.1 to 5% by mass; and
   a content of said ultraviolet scattering agent (C) is 2.5 to 30% by mass.

3. The cosmetic, according to claim 1, wherein:
   said nonionic surfactant (B) has an HLB value of not less than 9.

4. The cosmetic, according to claim 1, wherein:
   said nonionic surfactant (B) is a hydrogenated castor oil alkylene oxide condensate.

5. The cosmetic, according to claim 1, wherein:
   said water-soluble alkyl-substituted polysaccharide derivative (A) is hydrophobized hydroxypropyl methylcellulose.

6. The cosmetic, according to claim 1, wherein:
   said cosmetic is a sunscreen cosmetic.

* * * * *